United States Patent
Iyer

(10) Patent No.: US 8,821,731 B1
(45) Date of Patent: Sep. 2, 2014

(54) SYSTEMS AND METHODS FOR REGENERATING LIQUID SOLVENTS USED IN THE REMOVAL OF ORGANIC CONTAMINANTS FROM GASEOUS MIXTURES

(71) Applicant: Subramanian Iyer, Yorba Linda, CA (US)

(72) Inventor: Subramanian Iyer, Yorba Linda, CA (US)

(73) Assignee: Subramanian Iyer, Yorba Linda, CA (US)

( * ) Notice: Subject to any disclaimer, the term of this patent is extended or adjusted under 35 U.S.C. 154(b) by 0 days.

(21) Appl. No.: 14/271,398

(22) Filed: May 6, 2014

Related U.S. Application Data

(63) Continuation-in-part of application No. 13/530,339, filed on Jun. 22, 2012.

(60) Provisional application No. 61/820,647, filed on May 7, 2013.

(51) Int. Cl.
  *B01D 53/14* (2006.01)
  *C07C 41/34* (2006.01)
  *C07C 17/38* (2006.01)

(52) U.S. Cl.
  CPC ............. *C07C 41/34* (2013.01); *C07C 17/38* (2013.01)
  USPC .......... 210/651; 210/748.01; 95/196; 95/205; 95/206; 95/46

(58) Field of Classification Search
  None
  See application file for complete search history.

(56) References Cited

U.S. PATENT DOCUMENTS

| | | | | |
|---|---|---|---|---|
| 7,785,480 | B2 * | 8/2010 | Mak et al. | 210/798 |
| 2004/0206242 | A1 * | 10/2004 | Wijmans et al. | 96/234 |
| 2005/0061149 | A1 * | 3/2005 | Nieuwenhuizen et al. | 95/196 |
| 2010/0229720 | A1 * | 9/2010 | Sonwane et al. | 95/46 |
| 2011/0127218 | A1 * | 6/2011 | Reddy et al. | 210/640 |
| 2012/0058016 | A1 * | 3/2012 | Bansal | 422/168 |
| 2012/0211421 | A1 * | 8/2012 | Self et al. | 210/640 |
| 2013/0139695 | A1 * | 6/2013 | Chang et al. | 96/235 |
| 2013/0343978 | A1 * | 12/2013 | Ballaguet et al. | 423/242.1 |

FOREIGN PATENT DOCUMENTS

| | | |
|---|---|---|
| DE | 3813072 A1 | 12/1988 |
| DE | 4136344 A1 | 5/1993 |
| EP | 0442078 A1 | 8/1991 |
| EP | 0955352 A1 | 11/1999 |
| EP | 1316350 A1 | 6/2003 |

* cited by examiner

*Primary Examiner* — Duane Smith
*Assistant Examiner* — Pankti Patel
(74) *Attorney, Agent, or Firm* — Vito A. Canuso, III

(57) ABSTRACT

A method is provided of regenerating solvents used to remove gaseous contaminants from gaseous mixtures of various compositions with significantly reduced energy required, where one exemplary method includes directing a solution with the solvents and the preferentially absorbed and/or dissolved gaseous contaminants through a filter comprising a membrane having pre-determined diffusion rates so that a substantial portion of the gaseous contaminants pass through the filter, permitting the passage of the gaseous contaminants through the membrane for further processing, and recirculating the separated solvent so that it may be used again to remove new gaseous contaminants. In some cases, it may be desired to permit some of the solvent to pass through the membrane along with the gaseous contaminant.

1 Claim, 7 Drawing Sheets

SYSTEMS AND METHODS FOR REGENERATING LIQUID SOLVENTS USED IN THE REMOVAL OF ORGANIC CONTAMINANTS FROM GASEOUS MIXTURES

RELATED APPLICATION

This application is a continuation-in-part that claims priority to non-provisional patent application U.S. Ser. No. 13/530,339, filed Jun. 22, 2012, entitled System For Removal Of Organic Contaminants From Bio-Gas For Renewable Energy Production, and also claims priority to provisional patent application U.S. Ser. No. 61/820,647 filed May 7, 2013, the entire contents of both of which is incorporated herein by reference.

FIELD OF THE INVENTION

The embodiments herein relate generally to a system for removing contaminants from mixtures of gases as well as effluent and discharge gas flows and, more specifically, to the removal of impurities from bio-gas and natural gas for conversion to pipe-line quality natural gas.

BACKGROUND

Raw natural gas comes from three types of wells: (1) oil wells—natural gas that comes from oil wells is typically termed 'associated gas'. This gas can exist separate from oil in the formation (free gas), or dissolved in the crude oil (dissolved gas); vast amounts of gases are produced as a by-product of the crude stabilization process, and often disposed of using flaring or re-injected; and (2) gas wells and (3) condensate wells—natural gas from gas and condensate wells, in which there is little or no crude oil, is termed 'non-associated gas'. Gas wells typically produce raw natural gas by itself, while condensate wells produce free natural gas along with a semi-liquid hydrocarbon condensate.

Whatever the source of the natural gas, once separated from crude oil (if present) it commonly exists in mixtures with other hydrocarbons; principally ethane, propane, butane, and pentanes. In addition, raw natural gas contains water vapor, hydrogen sulfide (H2S), carbon dioxide, helium, nitrogen, and other compounds. While the ethane, propane, butane, and pentanes must be removed from natural gas, this does not mean that they must be wasted. In fact, associated hydrocarbons, known as 'natural gas liquids' (NGLs) can be very valuable by-products of natural gas processing. NGLs include ethane, propane, butane, iso-butane, and natural gasoline. Today it is commonly processed and fractionated into (i) methane (residue gas), or (ii) methane (residue gas), ethane, propane and butane (LPG) and condensate (C5+).

Natural gas processing consists of separating all of the various hydrocarbons and fluids from the pure natural gas, to produce what is known as 'pipeline quality' dry natural gas. The resulting NGLs are sold separately and have a variety of different uses; including enhancing oil recovery in oil wells, providing raw materials for oil refineries or petrochemical plants, and as sources of energy.

In a general trend to save and conserve the valuable energy resources of current oil fields, and eliminate flaring, the associated gases are being collected and processed as natural gas liquids (NGL) for sale in more and more oil fields around the world, both onshore and offshore fields. Major transportation pipelines usually impose restrictions on the make-up of the natural gas that is allowed into the pipeline. That means that before the natural gas can be transported it must be purified.

The actual practice of processing natural gas to pipeline dry gas quality levels can be quite complex, but usually involves four main processes to remove the various impurities: Oil and Condensate Removal, Water Removal, Separation of Natural Gas Liquids, and Sulfur and Carbon Dioxide Removal. Present methods of removal of hydrogen sulfide, for example, include employing an iron sponge or Sulfatreat™.

In addition to the four processes above, heaters and scrubbers are installed, usually at or near the wellhead. The scrubbers serve primarily to remove sand and other large-particle impurities. The heaters ensure that the temperature of the gas does not drop too low. With natural gas that contains even low quantities of water, natural gas hydrates have a tendency to form when temperatures drop. These hydrates are solid or semi-solid compounds, resembling ice like crystals. Should these hydrates accumulate, they can impede the passage of natural gas through valves and gathering systems. To reduce the occurrence of hydrates, small natural gas-fired heating units are typically installed along the gathering pipe wherever it is likely that hydrates may form.

As well as the impurities discussed above, landfills and sewage treatment plants contain carbon dioxide, hydrogen sulfide, volatile organic sulfides and siloxanes. Waste from industrial and domestic source is often discharged into landfill sites and sewage treatment plants, along with a variety of biological organic matter. The organic matter in the waste decomposes to produce bio-gas containing various volatile organic compounds, such as methane, carbon dioxide, hydrogen sulfide and volatile organic compounds, such as siloxanes, organic halides and organic sulfides. The bio-gas can be used to fuel various combustion engines to produce power, or both heat and power. However, the bio-gas from landfill sites and sewage treatment plants is contaminated with siloxanes. When an engine burns siloxane-contaminated bio-gas, the siloxanes, on oxidation, forms precipitates of silicon dioxide. The precipitates are deposited on engine parts such as turbine blades, pistons, cylinders, heat exchangers and emission control equipment. The deposits increase the abrasion of engine surfaces, leading to a loss of engine efficiency and premature engine failure. The deposits also poison catalytic converters in emission control equipment. Similarly, the combustion products of organic sulfides and hydrogen sulfides are corrosive in nature, requiring increased maintenance and replacement of corroded parts like cylinder heads, pistons, turbine blades and wheels. It is desirable to remove these contaminants prior to the bio-gas entering the combustion chamber of the power generation system.

According to the EPA's most recent data (2007), the U.S. has over 1,700 active landfills. Though the number of landfills has significantly decreased over the last 20 years, the average size of landfills has increased. Landfill sites produce methane and carbon dioxide gases due to the natural decomposition of solid waste material. Solid waste landfills are the second largest source of human-related methane emissions in the United States, accounting for approximately 23 percent of these emissions in 2007. In fact, these methane emissions from landfills represent a lost opportunity to capture and use a significant energy resource. Instead of allowing landfill gas (LFG) to escape into the air, it can be captured, converted, and used as an energy source. Financial benefits and improved community relations now provide the landfill industry with multiple incentives to employ bio-gas conditioning systems in the management of these gases.

Similarly, approximately 14,000 wastewater treatment facilities (WWTFs) operate in the United States, ranging in capacity from several hundred million gallons per day (MGD) to less than 1 MGD. Roughly 1,000 of these facilities operate with a total influent flow rate greater than 5 MGD, but only 544 of these facilities employ anaerobic digestion to process the wastewater. Moreover, only 106 WWTFs utilize the bio-gas produced by their anaerobic digesters to generate electricity and/or thermal energy. If the remaining WWTFs were to install combined heat and power technologies, approximately 340 MW of clean electricity could be generated, offsetting 2.3 million metric tons of carbon dioxide emissions annually. These reductions are equivalent to planting approximately 640,000 acres of forest, or the emissions of approximately 430,000 cars.

Utilization of bio-gas conditioning systems provides landfills and WWTFs with an opportunity to collect and dispose of the high levels of methane found in landfill and WWTF digester gases. Currently, many landfills and WWTFs are using untreated gas containing impurities such as sulfur, chlorine, silicon and moisture, to generate power and fire boilers. This untreated gas can make existing equipment such as boilers, engines, fuel cells and turbines susceptible to increased damages, increased maintenance costs and shorter life spans.

Purification of gas mixtures comprising a hydrocarbon or nitrogen, and carbon dioxide can be done by absorbing the carbon dioxide in a suitable liquid, typically amines or glycols. The absorbing liquids, once saturated with carbon dioxide, are regenerated in a separate step by exposing them to higher temperatures and lower pressures, causing the absorbed carbon dioxide to volatilize and separate out. This technique is used for purification of bio-gas methane from its contaminating carbon dioxide, as well as in coal burning plant effluents for carbon dioxide sequestration. The capital and running costs of such purification plants tend to increase rapidly with increasing concentration and volumes of carbon dioxide. However, liquids employed as absorbents tend to be corrosive, and thus relatively high maintenance costs are typically associated with such plants. Accordingly, other methods of separating hydrocarbons from carbon dioxide have been used. Among such other methods are those involving liquefaction of the gas mixture and fractional distillation of the liquid to produce a product vapor fraction relatively lean in carbon dioxide.

Fractional distillation has also been employed to separate a mixture of various hydrocarbons in a natural gas stream. Thus, the natural gas stream may contain methane with various proportions of ethane, propane, butane, pentane and hexane (commonly called $C_2$-$C_6$ hydrocarbons), as well as other higher hydrocarbons, commonly termed Natural Gas Liquids (NGLs). Cryogenics, employed in conjunction with fractional distillation, enables condensation of the $C_2$-$C_6$ components, with or without pressure, and then step-wise distillation of the desired component, based on its boiling point at the said operational pressure. This process is commonly employed in the oil and gas industry, especially for removal of the higher value NGLs from the lower value natural gas (mainly methane, $CH_4$), the latter being sent to the pipeline as the commonly available natural gas, with a calorific value of 950-1000 Btu/scf.

Pressure swing adsorption (PSA) is a known method of separating the components of a gaseous mixture by passage through a bed of adsorbent that preferentially adsorbs at least one component under pressure. A gaseous product that is relatively lean in the adsorbed component(s) passes out of the bed. The bed is regenerated by subjecting it to a lower pressure thereby desorbing the previously adsorbed component(s). The adsorbent is generally a molecular sieve, e.g. a zeolite or carbon molecular sieve. In more efficient commercial PSA processes, a plurality of beds is employed and the incoming gas stream for separation is switched between the beds so as to facilitate the continuous supply of gaseous products.

The equilibrium quantity of a gas adsorbed on a molecular sieve is not solely a function of pressure but also one of temperature. Indeed, some commercial gas separation processes effect separation by temperature swing rather than pressure swing. Although typical zeolite molecular sieves have gaseous adsorption equilibrium values that are achieved rapidly and then remain constant with time, carbon molecular sieves exhibit dynamic sieving behavior before coming to equilibrium (the former effects the separation); both kinds of sieves increase in temperature as gas is adsorbed since heat of adsorption is liberated, and decrease in temperature again when gas is desorbed. These changes in temperature are substantially equal. There is, however, an additional increase in temperature as a result of the compression of the incoming gas mixture for separation. A substantial proportion of the heat of compression is removed in an after cooler that is conventionally associated with the compressor. There is also a reduction in temperature associated with the reduction in pressure during the desorption step. It might be expected that the PSA process would therefore run at an average temperature below ambient in view of there being net refrigeration that is produced by the pressure reduction required to effect the desorption step. In practice, however, only a relatively small proportion of the refrigeration developed during the desorption step is employed to reduce the temperature of the bed of adsorbent, and most of the refrigeration generated during desorption is wasted in the gas that is vented to the atmosphere. Thus, in practice, the average temperature at which the pressure swing adsorption process operates is usually above rather than below ambient temperature. Because the equilibrium amount of gas that is adsorbed increases with decreasing temperature, the failure to efficiently use the refrigeration generated leads to unnecessarily high specific power consumption. Moreover, the temperature rise that takes place during adsorption is also undesirable since lower temperatures generally favor adsorption. The temperature fall that takes place during desorption is similarly undesirable since in general higher temperatures favor desorption.

$H_2S$, hydrogen sulfide, a common contaminant of bio-gas from landfills and anaerobic digester plants, as well as in some natural gas streams, is commonly removed from the gas stream by absorption into granular iron or sponge iron powder, or similar alloyed media. The hydrogen sulfide chemically reacts with the iron in the media to form iron sulfide, and leaves a gas stream substantially purified of the sulfide contaminant and thus less corrosive to combustion processes like power-plants for energy generation. The granular iron sulfide, however, cannot be regenerated without a substantial energy penalty, and is commonly disposed of in a landfill. Other methods for $H_2S$ removal include hydrodesulfurization (HDS), which involves use of hydrogen gas with catalysts for removal of the sulfide species.

All the above processes are either energy intensive, or consume raw materials which cannot be easily regenerated. Cryogenics and fractional distillation are prohibitively energy intensive for small-scale plants, while pressure and temperature swing adsorption (PSA and TSA) are prohibitively expensive for large-scale plants, and energy intensive for small-scale plants. HDS is commonly used in petroleum refineries, and is especially suitable only for large-scale plants. The present invention reflects efforts to solve at least some if not all of the above problems.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
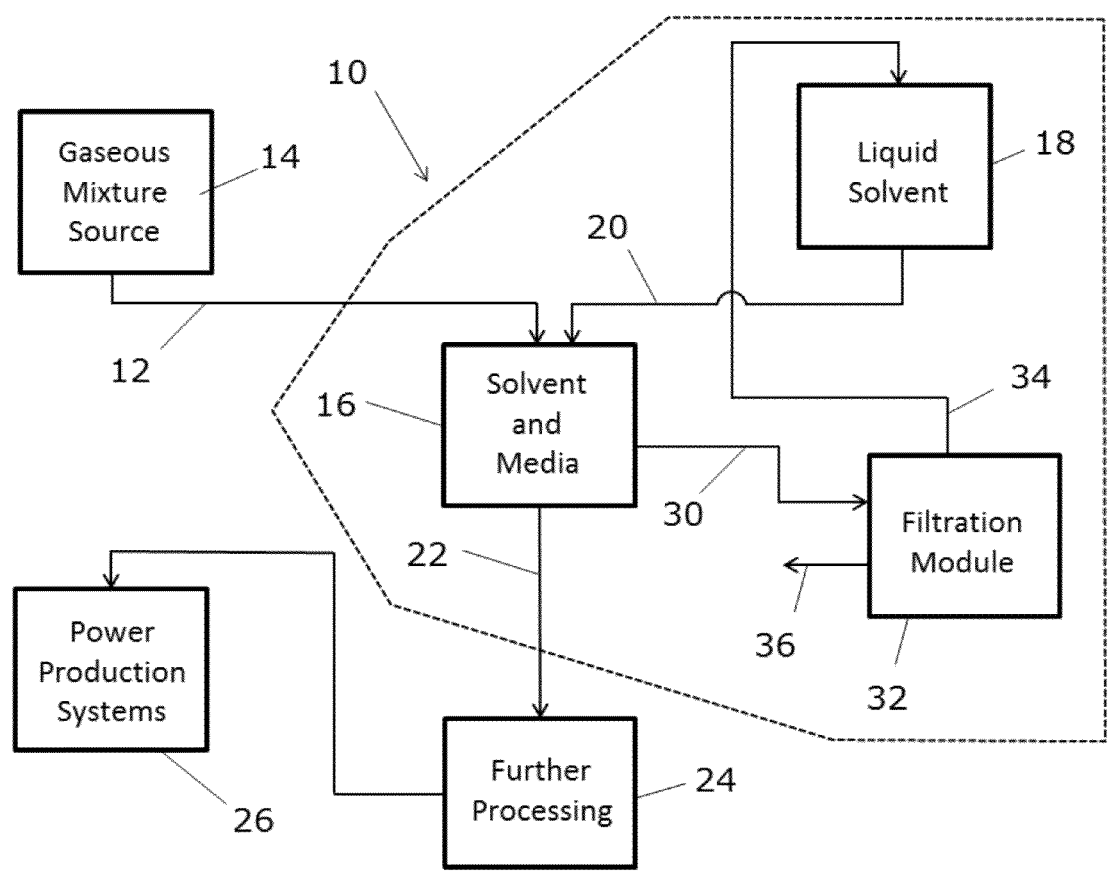
FIG. 1 is a schematic of one embodiment of a reactor system of the present invention as applied to a source of gaseous mixture from which it is desired to remove gaseous contaminants.

Embodiments of the present invention comprise one or more of three otherwise distinct processes employed in unique arrangements to scrub contaminants from hydrocarbon effluent gases (bio-gas) that results in enhanced and useful energy generation from the effluent gases. In certain embodiments, the three processes comprise absorption using a liquid medium, polymerization using a solid catalyst and separation using filtration. Variations on each are contemplated, however, including the phase of the media and/or catalyst and the type of filtration or separation mechanism.

With regard to the process of absorption, while solid-phase or gas-phase scrubbing can be effective, it is preferred that a liquid-phase solvent be employed; i.e., liquid at standard temperature and pressure. The preferred solvent should have a high boiling point, preferably in excess of 200° C., and appreciably low vapor pressures, to minimize loss of the liquid solvent during gas scrubbing operations. Where the contaminant at issue is siloxane, the solvent should exhibit high siloxane solvation tendencies, resistance to peroxide formation, and chemical resistance to degradation or polymerization in acidic or basic environments. The preferred solvent should be a low molecular weight liquid because nano-filtration membranes separate liquid components based upon molecular weight and size constraints, typically allowing permeation of molecules of size lesser than 300 Daltons (Da), but retaining larger molecules.

In certain embodiments of the invention, the absorption solvent comprises an organic liquid having a molecular weight of less than 300 Daltons, with inherent chemical stability towards catalysts, acids and bases, to physically absorb the organic contaminants at issue. In the case of siloxanes, certain ethers comprising dialkyl terminated glymes are preferred, including butyl diglyme (diethylene glycol dibutyl ether), ethyl glymes, ethyl diglymes, triglyme and tetraglyme, hexyl ether, anisole, dibenzyl ether, but also polyethylene glycols and propylene glycols are contemplated, as well as compounds such as butyl glycol ether acetates or methoxy propyl acetates (also known as propylene glycol methyl ether). With the latter two solvents, a propensity for peroxide formation over time may be inhibited with agents like 2,6-di-tert-butyl-para-cresol (2,6-BHT). Those compounds with acetate groups at their ends may render the solvents prone to polymerization themselves in acidic or basic environments. Similarly, solvents with hydroxyl groups at their ends are less suitable, because the hydroxyl groups render them prone to polymerization themselves in acidic or basic media.

A preferred solvent, butyl diglyme, is end-capped with butyl groups, and unlike other methyl end-capped glymes, is not miscible with water. The high flash point of butyl diglyme renders it safe for use in industrial applications, and it is not generally considered a volatile organic compound (VOC), thus providing an environmentally friendly solvent. Its boiling point is 256° C., while its water solubility is only 0.3 mg/liter. Butyl diglyme is stable in both acidic and basic environments. Similar solvents, like tetraethylene glycol dimethyl ether, polyethylene glycol dimethyl ether or dipropylene glycol dimethyl ether, can also be used for the purposes described herein, though their water miscibility is higher than for butyl diglyme. These glyme solvents have no free hydroxyl functionality, and thus are exceedingly stable in polymerization reactions, acting both as carrier molecules, as well as phase-transfer catalysts. A mixture of glymes may also be used, particularly where both polar and non-polar siloxane contaminants exist in the bio-gas, depending on the concentration of each.

Recognizing the regeneration of the solvent is desirably from an energy efficiency standpoint, and contemplating filtration as one means of achieving separation of the solvent for recirculation, it is contemplated that an inventive combination with the absorption process is to polymerize the contaminants, such as the siloxanes, so that during filtration, the liquid solvent employed may be separated from the solubilized and polymerized contaminants due to the larger molecular size of the contaminants. Any component that is too large in size will not pass through the membrane of a filter, such as polymerized siloxane contaminants. In that regard, significant research effort was spent evaluating various candidates of solvents to find those that dissolved contaminants such as siloxanes (having a range of polarities), were non-volatile, were of small-enough molecular size to pass through filtration for purposes of regeneration, did not inhibit polymerization of the contaminants, and did not degrade on the presence of the polymerizing catalyst.

Embodiments of the invention preferably comprise the use of acidic polymerizing catalyst. As both landfill gas and wastewater digester gas are significantly contaminated with carbon dioxide, use of basic catalysts would lead to catalyst degradation or poisoning, due to formation of basic carbonate salts. Acid-catalyzed condensation of silanol and silyl ether groups is an important reaction leading to the formation of the siloxane bond. With cyclosiloxanes, the monomer ring is involved in both the initiation and the propagation steps of polymerization. Ring-opening polymerization is a form of chain-growth polymerization, in which the terminal ends of a polymer acts as a reactive center, where further cyclic monomers join to form a larger polymer through ionic propagation. The treatment of some cyclic compounds with catalysts brings about cleavage of the ring, followed by polymerization to yield higher molecular-weight entities. Similarly, linear siloxanes can be added to the chain by redistribution polymerization techniques. Thus, both cyclic siloxanes and linear siloxanes can be polymerized to polyorganosiloxanes by ring-opening polymerization and/or redistribution polymerization. The polymerization can be carried out by the anionic route, via basic catalysts, or the cationic route, via acid catalysts.

It is preferable to use solid-state or non-volatile liquid acid catalysts, via the cationic route, as they enable easier separation of the catalysts from the liquid solvents and the solvated siloxane molecules. The use of a solid-state catalyst packed bed also increases the probability of several siloxane molecules coming into contact with each other for polymerization to occur, due to the higher concentration of these molecules in the densely-packed catalyst bed.

The strongly acidic family of sulfonic and phosphonic acid compounds are readily available, proven to polymerize volatile siloxane monomers to nonvolatile oligomers and polymers, and are available commercially as polymer-bound resins. In particular, sulfonic acid, like sodium polystyrene sulfonate, or phosphonic acid resin-based solid-state catalysts are preferred for polymerization of the siloxanes to high molecular-weight silicone polymers like organosiloxanes or PDMS. One example of a suitable acidic resin catalyst is Monosphere® M-31 ion exchange resin by Dowex®, where the sodium ions have been replaced by $H^+$ ions. These are strongly acidic cation exchange resins, with a wet volume capacity, in the H form, of 1.91 meq/mL and a mean particle size of 500 microns. The [—SO3H] groups are fixed on a solid support, and thus cannot move around as in homogeneous media. The use of such solid acid catalyst resins, with a liquid solvent for sequestering and polymerizing volatile siloxanes in landfill or digester gas, results in a three-phase reaction volume of solid-liquid-gas interaction in the proposed invention.

Regeneration of the liquid solvent is advantageous for the techno-economic viability of siloxane removal. One cost effective means for the separation of low molecular weight liquid solvents from higher molecular weight siloxane solutes is nano-filtration (NF), using solvent-stable membranes, which are capable of filtering out molecules with a size greater than 300 Daltons (Da), a cutoff size greater than the molecular size of the solvent itself. It is contemplated that other filtration-separation systems may be employed depending upon the solvent media and polymerization catalyst, including ultrafiltration, reverse osmosis, and forward osmosis, among other systems. In the case of a siloxane removal embodiment employing, for example, butyl glyme as the solvent, NF purification and regeneration of the liquid absorbent is preferably the low-energy pathway. The use of solid-state catalysts advantageously avoids interfering or destabilizing the membranes used in nano-filtration, although liquid-phase polymerization catalysts may also be employed if the membrane materials are inert to them.

With regard to the NF embodiments, it is preferred that a membrane comprising a molecular weight cutoff of 300 Da be employed so that smaller molecular weight siloxanes are not filtered out or separated from the solvent. These unseparated siloxanes may preferentially serve as seed molecules for polymerization to occur in the packed bed catalysts, as described earlier.

Embodiments of the present invention comprise a process for the removal of various contaminants from a gaseous mixture, either alone or together, by a liquid scrubbing process, either at low or high pressures, followed by a liquid membrane separation process, whereby the contaminating species is removed and the liquid media is regenerated at low energy expenditures.

Referring to FIG. 1, application of one embodiment 10 of the present invention to bio-gas contaminant separation may be appreciated. In that regard, in the context of treating, for example, landfill (effluent) bio-gas 12 from a landfill 14 (or wastewater treatment plant), embodiment 10 comprises a system 16 for absorbing contaminants in the landfill gas 12 and sequestering the contaminant using specific processes unique to the contaminant being sequestered. Solvent 18 is provided to system 16 via delivery line 20. One embodiment of the invention comprises a solvent from the group consisting of butyl diglyme or other similar glymes or other non-protic solvents capable of dissolving linear and cyclic siloxanes, and more preferably, solvents from the family of dialkyl terminated glymes. The reactor is configured to permit a suitable physical interaction between the solvent and the effluent landfill gas discharge from the landfill, which includes contaminated organic material that should be removed prior to use in power generation equipment. The landfill effluent gas may be directed into reactor 16 under high pressure, so the reactor is preferably configured to withstand high pressures. For other contaminant species, different solvents can be used, specific to the targeted species being removed. Thus, for removal of oxygen or nitrogen from the inlet gas, perfluorodecalin can be used as a solvent for oxygen or nitrogen. For removal of carbon dioxide, various polyglycols, like Dow Chemical's Selexol, or various hydrophobic or hydrophilic glymes can be used, like polyethylene glycol dibutyl ether or tetraethylene dimethyl ether, respectively, For removal of hydrogen sulfide gas as the contaminant, tetraethylene glycol dimethyl ether or triethylene glycol dibutyl ether can be used as one of the preferred solvents.

Membrane 32 is preferably a nano-filtration membrane with a pore size greater than the molecular weight and size of the solvent species. Since the solvent molecules are much bigger in size as compared to the gaseous contaminant dissolved in the solvent, the gaseous contaminant preferentially passes through the pores of the nano-filtration membrane, along with some quantity of the solvent, which acts as a carrier agent for the contaminant species, based on the pressures being used in the nano-filtration process. Alternatively, a pervaporation membrane, with a preferential permeability only for the contaminant species can be used to separate the contaminant species completely from the solvent molecules. Most of the solvent is thus purified of the contaminant species, enabling re-use in system 16. Stream 36 consists either of the contaminant with some associated solvent, or the contaminant by itself, depending on the membrane used. Such a system is much less energy-intensive, as compared industry techniques for desorbing the contaminant species from its solvent by application of heat to regenerate the solvent and physically separate the contaminant species. Membranes used typically would be inert to the solvents to be used, and thus organo-philic in nature, enabling longer membrane life and decreased break-through of solvents or other contaminant species.

In one embodiment, the invention comprises reactor 16 housing the organic solvent flowing through a solid state media to permit interaction between the solvent and any contaminants within the effluent gas. The treated effluent gas 22 discharged from reactor 16 may be directed for further processing (e.g., passing through an activated carbon filter 24) or for release into the inlet of downstream power generation equipment 26. For purposes of regenerating the liquid solvent, one embodiment of the present invention further comprises discharge line 30 from reactor 16 containing the solvent and absorbed or dissolved contaminant species, which is directed to a means for separating the solvent from the contaminant species, such as a pervaporation module or nano-filtration module 32. The separated solvent 34 may then be directed to the solvent supply 18 for supply to reactor 16 as needed. The separated contaminants 36 separated by the nano-filtration system 32 may be disposed in any fashion desired.

Figure 2:
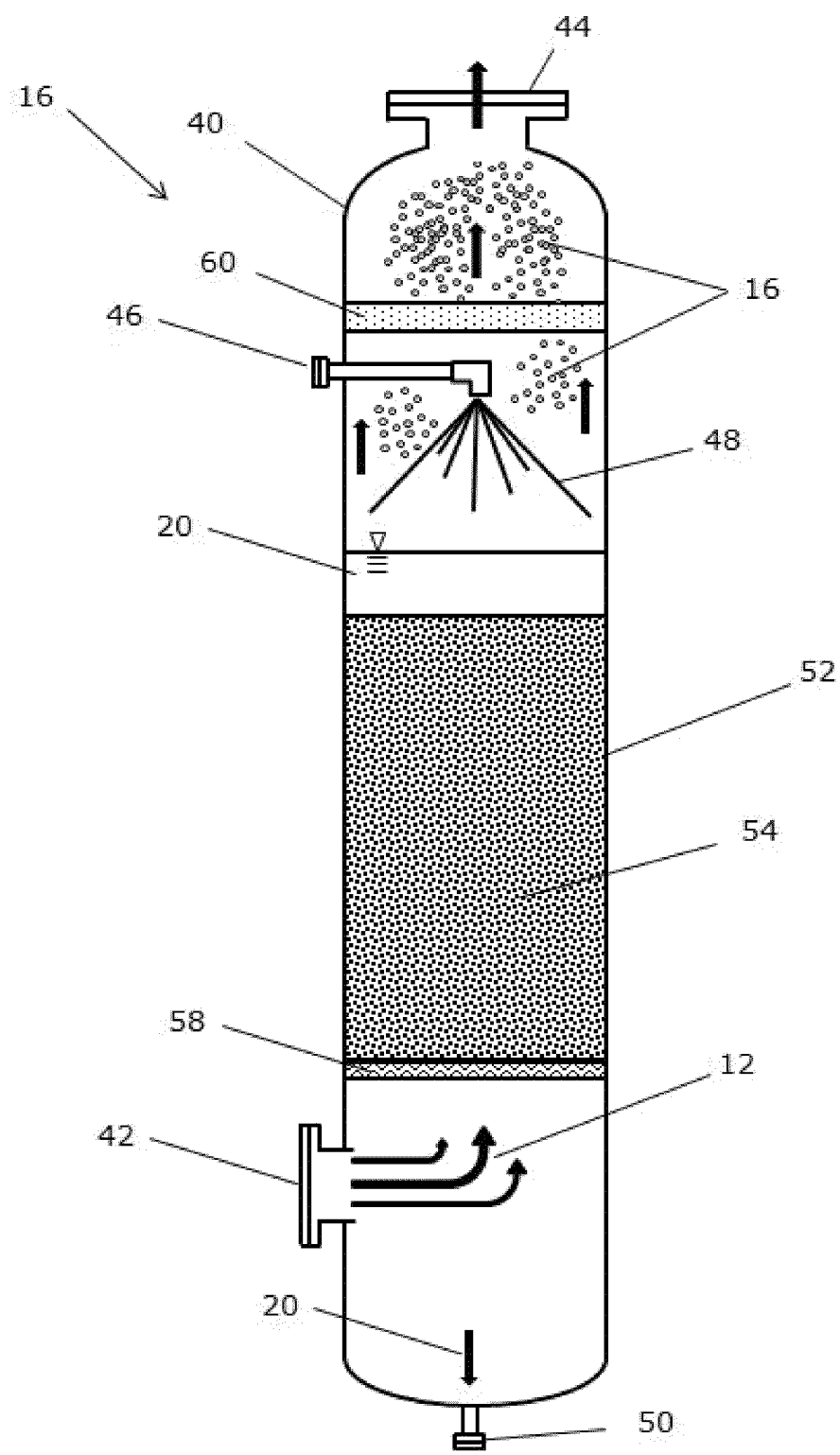
FIG. 2 is a schematic of one embodiment of a reactor in a reactor system of the present invention.

Referring to FIG. 2, one embodiment of the present reactor may be described. In that regard, reactor 16 comprises a housing 40, preferably a high pressure housing in case effluent gas is delivered above ambient pressure. The reactor housing 40 comprises an inlet 42 for the introduction of effluent gas 12 from, for example, the landfill, and an outlet 44 for the discharge of treated effluent gas for further treatment or to power production systems (see FIG. 1). Housing 40 further comprises an inlet 46 for the introduction of solvent 20 from the solvent supply 18 (FIG. 1). The solvent 20 is preferably sprayed 48 into the interior of the reactor housing 40 to enhance contact with the effluent gas, as explained further below. The reactor housing 40 further comprises an outlet 50 for the circulation of solvent and polymerized contaminants to the separation mechanism, such as the nano-filtration system 32 (FIG. 1).

In a preferred embodiment of reactor 16, a packed bed 52 of solid state media 54 is supported above a mesh support 58 within the reactor housing 40, which further comprises a mesh 60 above the solvent inlet 46 to preclude the inadvertent discharge of the solid state media 54 from the reactor 16. In one application of the reactor 16 for treating siloxanes, the solid state media comprises a polymerizing catalyst 54 comprises a packed bed of Monosphere® M-31 ion exchange resin, which is fully immersed in the solvent 20, which preferably comprises a dialkyl terminated glyme, such as butyl diglyme, introduced into the reactor 16 at inlet 46. In operation, the effluent gas from the landfill is introduced at inlet 42 and directed upwardly through the packed bed of polymerizing catalyst 54 and bubbles upwardly 64 above the introduction of sprayed solvent 48, through mesh 60, and out through outlet 44 at the top of the reactor 16. The solvent 20 is sprayed 48 for thorough dispersion among the polymerizing media for interaction with the effluent gas passing through it in a counter-current passage, relative to the solvent used. The solvent 20 is re-circulated to replenish the reactor through outlet 50 at the base of the reactor 50. It should be noted that an embodiment of the reactor may house the catalyst media so that it is wetted by the solvent within the reactor.

Figure 3:
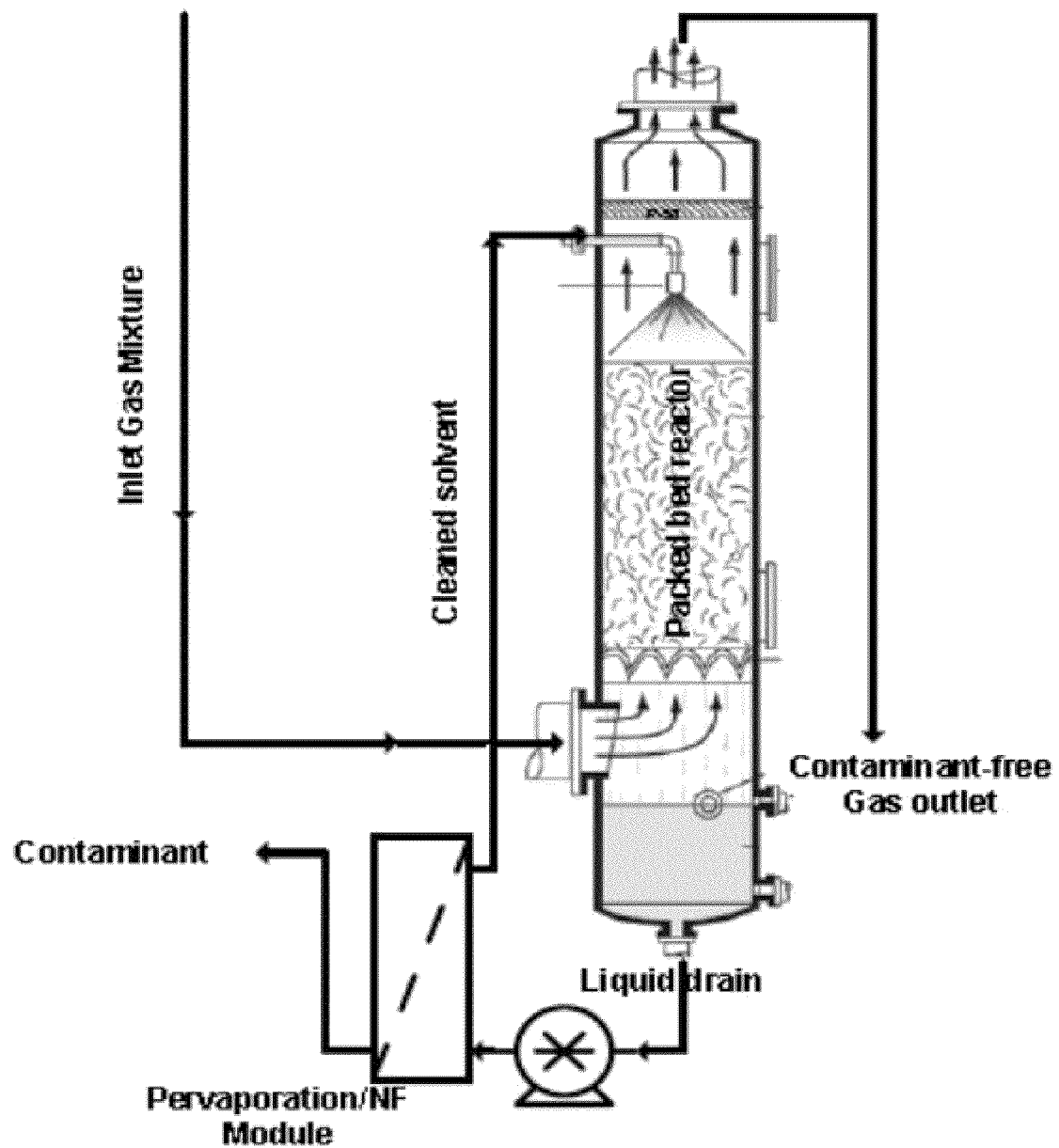
FIG. 3 is a schematic of one embodiment of a reactor system of the present invention as applied to a source of gaseous mixture from which it is desired to remove gaseous contaminants.

Referring to FIG. 3, one embodiment of a system for removing contaminant species from a gaseous mixture at significantly reduced energy levels is presented. The system comprises a liquid solvent scrubbing vessel for receiving and scrubbing the inlet gas mixture, and for receiving liquid solvent. The scrubbing vessel is preferably one such as the reactor described in FIG. 2, although it may be of other types as well. In one embodiment, the scrubbing vessel comprises a packed bed reactor configured so that the gaseous mixture enters from the bottom or near the bottom while the solvent liquid enters from the top or near the top. The liquid solvent is then preferably showered down upon the uprising gaseous mixture. The solvent selected is preferably applicable to the targeted gaseous contaminant so that the gaseous contaminant is absorbed and/or diffused into the solvent. The scrubbing vessel preferably comprises solid-state media for optimizing the mixing and contact of the gaseous mixture and the liquid solvent.

Once the gaseous contaminant is sufficiently dissolved or absorbed by the solvent, original gaseous mixture, with the substantially removed contaminant, is discharged from the vessel either into the air or for further processing. Likewise, the solution comprising the solvent and the gaseous contaminant is directed out of the scrubbing vessel for regeneration of the solvent. In that regard, embodiments of the present system further comprise a filter, or membrane module, for separating and regenerating the solvent for purposes of recycling the solvent. In the case of the desired removal of some gaseous contaminants, a pervaporation filter may be used with a membrane of specific diffusion rate sufficient to permit the passage through of substantially all of the gaseous contaminant while precluding the passage of substantially all of the solvent. In the case of the desired removal of other gaseous contaminants, a nano-filtration module may be used with a membrane of specific pore size sufficient to permit the passage therethrough of substantially all of the gaseous contaminants and a certain amount of solvent for purposes of keeping the gaseous contaminant diffused and/or absorbed within the solvent; i.e., in solution. Keeping the gaseous contaminant in solution post filtration facilitates the further processing of some gaseous contaminants, such as $H_2S$, as discussed below.

Proper selection of the liquid solvent enables removal of the particular contaminant targeted, based on the solvation capacity of the selected solvent for the specific contaminant species targeted. In addition, proper selection of the membrane enables no degradation during operation from the liquid solvent used. For example, with regard to the removal of carbon dioxide, preferred solvents comprise a hydrophilic glyme, such tetraethylene glycol dimethyl ether, in which the solubility of $CO_2$ amounts to 3.1 N cm3/g bar at 25° C., a hydrophobic glyme, such as polyethylene glycol dibutyl ether, with a solubility of $CO_2$: 2.8 N cm3/g bar at 25° C.), or polyglycols. For the removal of $H_2S$, polyethylene glycol dimethyl ether has an excellent selectivity for $H_2S$, as compared to absorption of $CO_2$ or methane in the same solvent.

For removal of oxygen from air, perfluorodecalin has an excellent selectivity for oxygen over nitrogen, enabling separation of oxygen and nitrogen from air mixtures. Oxygen, once absorbed in the solvent, in preference to nitrogen, can be subsequently desorbed by vacuum processes and collected as a substantially pure oxygen stream, while the nitrogen is also purified of oxygen and can be obtained as a substantially pure nitrogen stream. In that regard, a system such as that shown in FIG. 4, for example, could be used to preferentially separate oxygen from nitrogen, the latter of which would emerge as the effluent from the reactor, while the oxygen/solvent mixture emerges from the reactor for separation via the filter.

There exist several solvents, which have a high selectivity for ethane, propane, butane, heptane and hexane over methane molecules, thus enabling separation of these higher level hydrocarbons ($C_2$ through $C_6$ and higher hydrocarbons) from natural gas, leaving the main constituent of natural gas as methane. One example of such a solvent would be triethylene glycol dibutyl ether, which has a selectivity of the higher hydrocarbon gases over methane by a factor greater than 10 at atmospheric pressures. Use of higher pressures increases the selectivity ratio of these higher hydrocarbon gases over methane. Use of properly selected solvents can result in separation of the needed contaminant selectively from a gaseous mixture of various constituents, to result in a purified stream of the main gas constituent desired. Since most of these solvents are also mutually miscible in various proportions, such solvent mixtures can be used in a unitized system for removal of various contaminant species in a single pass.

Depending on the kinetic diameters and molecular weights of the gas contaminant, the molecular weight and molecular size of the liquid used, and the particular membrane employed, either pervaporation membranes or nano-filtration membranes can be used for efficient and low-energy regeneration of the liquid solvent and sequestration of the contaminant. The term pervaporation is a colloquial name for permselective evaporation; i.e., employment of a particular membrane selected to separate a gas from a liquid or a liquid from a liquid. The dissolved contaminants can now be separated from the solvent by using either organophilic pervaporation membranes or organophilic nano-filtration membranes, chemically stable to the solvents being used, and can now be sequestered and collected, or suitably converted to more desirable products in a separate down-stream process. Thus, $H_2S$ can removed from natural gas or bio-gas by such a system, and then be converted to elemental sulfur or alkali polysulfides in an additional downstream process, with the latter by-products having an intrinsic economic value in agriculture or for soil remediation. For volatile siloxanes, after removal and conversion to high-molecular weight cyclic polysiloxanes by ring-opening polymerization with suitable catalyst media, the converted siloxanes are rendered non-volatile and can be safely sequestered.

Similarly, $CO_2$ as a gas, separated by the above process, can be sequestered and either converted to dry ice or used for re-injection back into oil wells for improved oil flows. The $C_2$ through $C_6$ higher hydrocarbons separated from natural gas or associated gas can further be separated, in a down-stream process, into their individual components by fractional distillation and sold at their much higher intrinsic values, as compared to methane itself. Oxygen separated from nitrogen can be bottled and used for either medical purposes or for other industrial applications, while the nitrogen itself has industrial applications in cryogenics as liquid nitrogen or inert atmospheres for industrial use.

Figure 4:
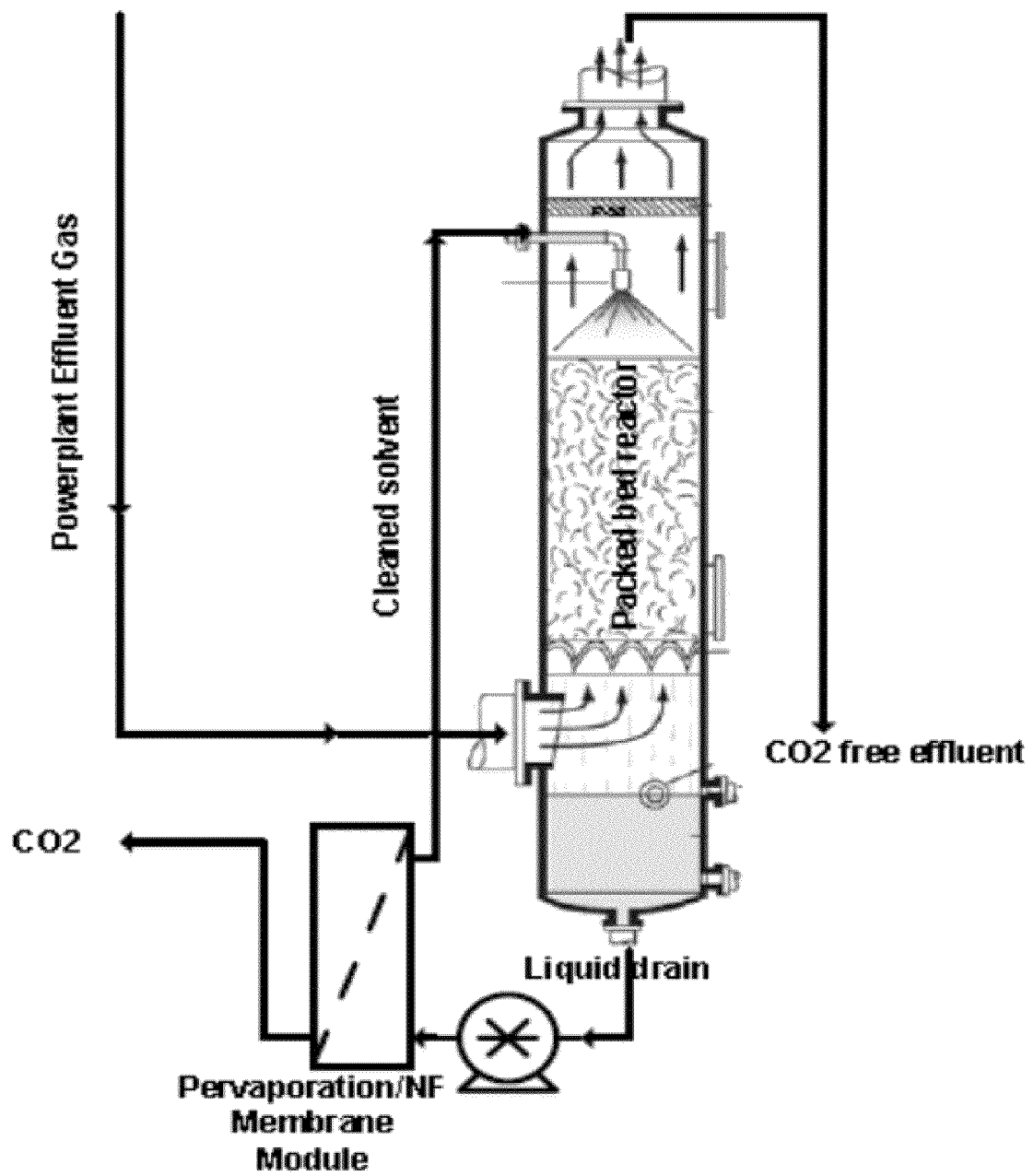
FIG. 4 is a schematic of one example of a reactor system for removing carbon dioxide as a gaseous contaminant from a gaseous mixture.

In one example process of contaminant removal, the method comprises the removal of carbon dioxide from, for example, power plant effluent or a bio-gas mixture, as reflected schematically in FIG. 4. Power plant effluent typically consists of $CO_2$, water vapor and nitrogen, with small amounts of other contaminants. It is of interest to remove the $CO_2$ from this effluent gas for sequestration purposes, and to reduce the build-up of $CO_2$ in the atmosphere to prevent continued global warming. The separated $CO_2$ is sequestered by physical means, like injection in salt caverns or injection into emptied oil and gas fields. Similarly, bio-gas normally consists of 45-55% methane, 45-55% $CO_2$ and the balance made up of contaminants like $H_2S$, siloxanes, $N_2$ and $O_2$. Typical calorific values for bio-gas of the above composition ranges around 45-550 BTU/scf. In cases where a higher BTU requirement is needed for the combustion engine, the $CO_2$ needs to be removed to increase the concentration of methane in the bio-gas.

Figure 5:
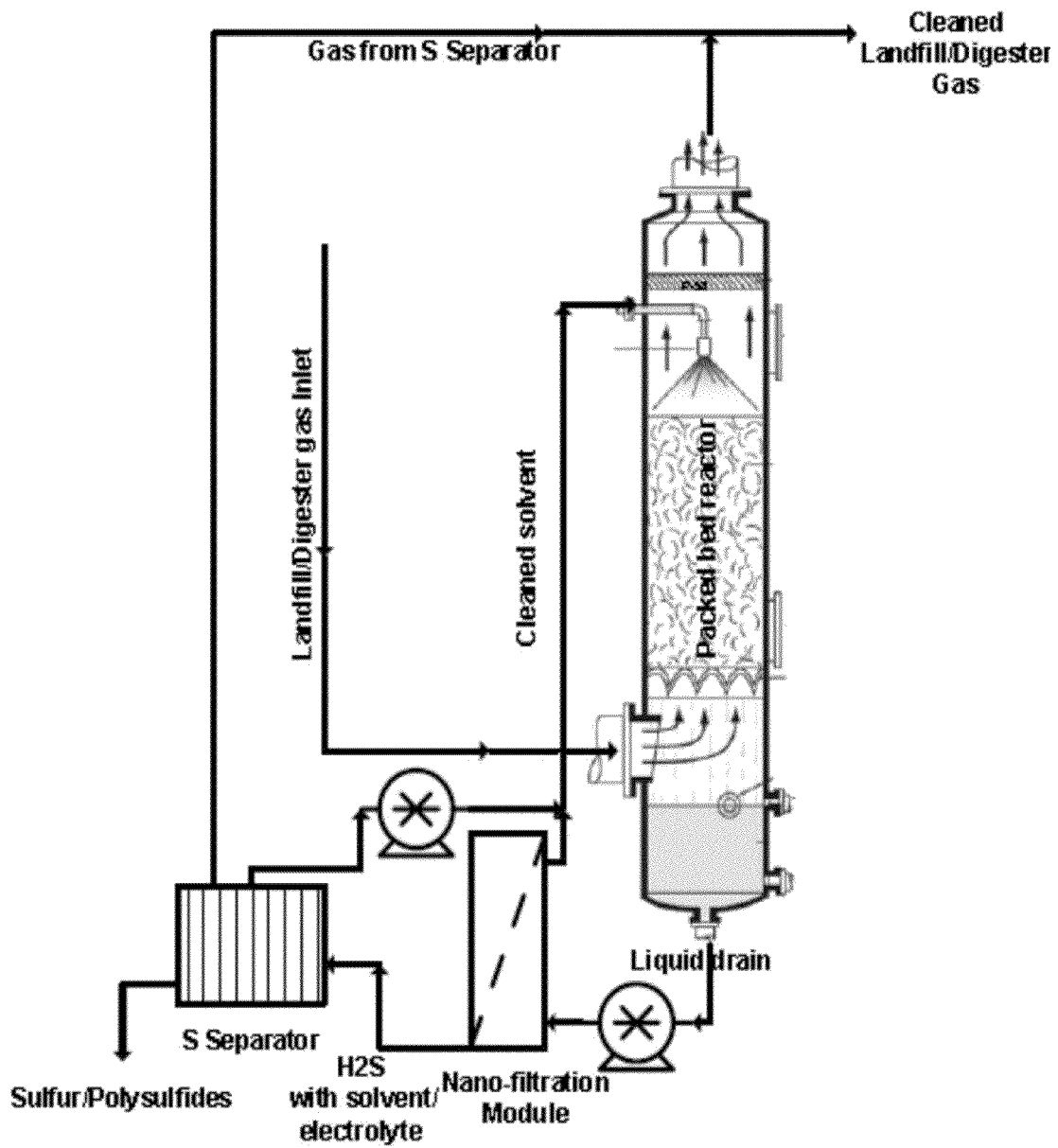
FIG. 5 is a schematic of one example of a reactor system for removing hydrogen sulfide as a gaseous contaminant from a gaseous mixture.

With regard to the removal of $H_2S$ from natural gas or bio-gas and its sequestration, reference is made to FIG. 5. $H_2S$ and other organic sulfides are normal constituents of both natural gas and bio-gas, and need to be removed before the combustion process to prevent formation of sulfur oxides, which can lead to equipment corrosion in the presence of moisture, or in acid rain.

An additional process after separation of the $H_2S$ and organic sulfides, with a calculated amount of the solvent, comprises electrolyzing the sulfide solution to convert the sulfides into elemental sulfur or alkali metal polysulfides in an electrochemical cell, as per the equation: $S+2H^++2e^- \leftrightharpoons H_2S$ ($E^0=0.14$ volts). The decomposition voltage for $H_2S$ in common electrolytes is around 0.25 volts, inclusive of any cell over-voltages. Thus, at extremely low power consumptions, $H_2S$ can be converted into either solid elemental sulfur or into sodium or potassium polysulfides. The expected electrolyzer operational points are at 0.5 volt and a current density of 3-5 amp/cm$^2$, with a coulombic efficiency greater than 90%. Both elemental sulfur and the polysulfides have applications in agriculture, soil remediation and in industrial applications. The preferred solvent in such an application would be tetraethylene glycol dimethyl ether (TGME), in which some salts have been dissolved to enhance electrochemical conductivity for the H2S electrolysis step described herein. TGME is very stable in electrochemical applications, having an electrochemical window of 3.5 volts in reduction-oxidation conditions, and also with a high solubility for $H_2S$ and organic sulfides. Such a step has advantages over current industrial processes like absorption of the $H_2S$ in iron sponge, or other processes like hydro-desulfurization, due to not having to deal with a waste product disposal in the case of iron sponge, or much lower energy consumption in the case of hydro-desulfurization, respectively.

Figure 6:
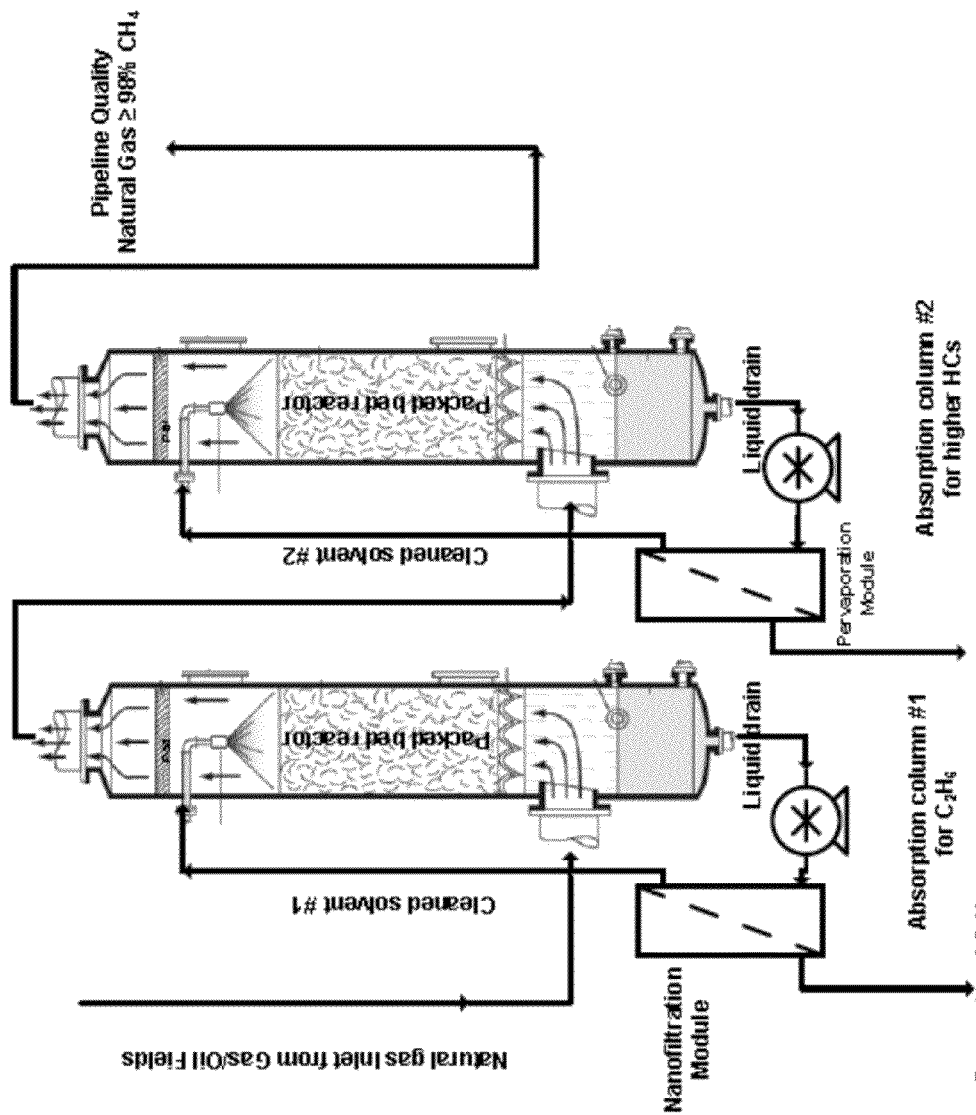
FIG. 6 is a schematic of one example of a reactor system for removing higher level hydrocarbons as a gaseous contaminant from a gaseous mixture.

With reference to FIG. 6, an example system and method for the removal of various hydrocarbon contaminants from natural gas may be described. Natural gas commonly contains methane, associated with various amounts of ethane, propane, butane, pentane, heptane and hexane (commonly termed $C_2$ to $C_6$ hydrocarbons). These higher hydrocarbons have a much higher market value than the methane in the natural gas, and where the gas flows are high enough to warrant economic removal and separation of these constituents, energy-intensive industrial processes like cryogenics and fractional distillation is used to segregate these higher hydrocarbons. Embodiments of the present invention reflect a significantly cheaper pathway to segregate these higher hydrocarbons from a natural gas stream.

Figure 7:
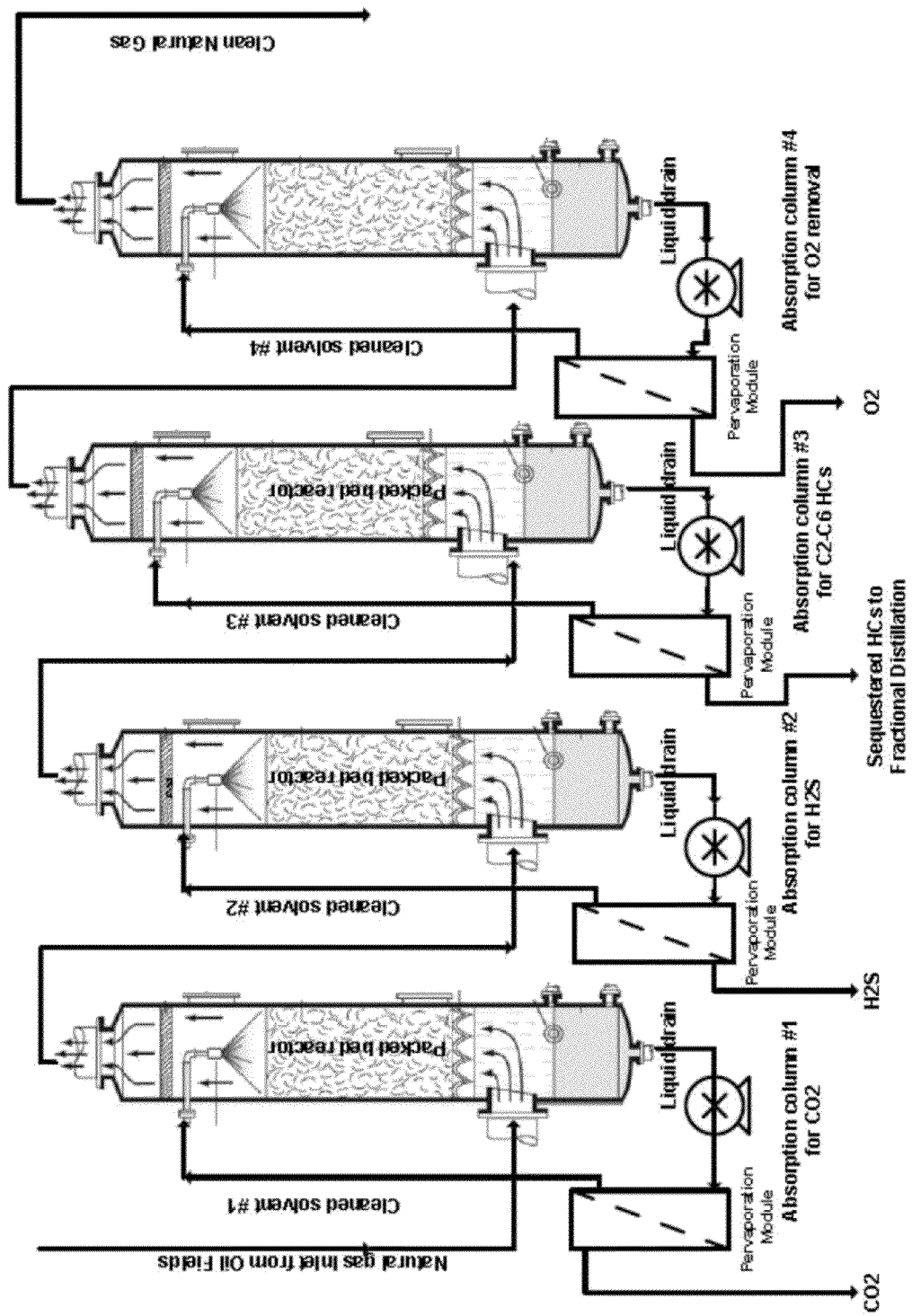
FIG. 7 is a schematic of one example of a unitized reactor system for removing several gaseous contaminants from a gaseous mixture.

It is contemplated that hydrocarbon gas emissions collected from landfills and digesters, for example, may be converted to pipe-line quality natural gas employing similar sub-systems described above. In that regard, hydrogen sulfide, carbon dioxide and oxygen may be removed from the landfill/digester gases to produce natural gas that is essentially 96% methane. Thus, it may be advantageous to provide a system and methodology that combines the ability to remove more than one gaseous contaminant from a gaseous mixture. For example, referring to FIG. 7, a unitized system for removal of various contaminants from natural gas may be described. In certain gas fields, in addition to the higher hydrocarbons, significant amounts of $CO_2$, $H_2S$, $O_2$ and other constituents may also be present. Since pipeline quality natural gas in the US specifies a composition of greater than 98% methane, as well as a calorific value in the range of 950-110 BTU/scf, these contaminants need to be removed from the inlet natural gas stream. FIG. 7 exhibits a sequential train of liquid scrubbers and membranes, with the solvents and membranes in each train chosen for the specific species to be removed.

It should be noted that the embodiments and variations described herein are presented only as examples, and other variations in configuration and materials may be utilized while enjoying the benefits of the invention herein. Thus, the scope of the invention is to be measured by the allowed claims below rather than the embodiments described herein above.

What is claimed is:

1. A method of regenerating solvents used to remove gaseous contaminants from gaseous mixtures with significantly reduced energy required, the method comprising:

directing a solution comprising the solvents and the preferentially absorbed and/or dissolved gaseous contaminants through a nano-filtration system comprising a membrane having pre-determined diffusion rates and having a pore size sufficient to permit at least some of the solvent to pass through the membrane so that the gaseous contaminant that passes through the membrane remains substantially absorbed and/or dissolved in solution and so that a substantial portion of the gaseous contaminants pass through the filter,
permitting the passage of substantially all of the gaseous contaminants through the membrane for further processing
recirculating the separated solvent so that it may be used again to remove new gaseous contaminants, and
electrolyzing a sulfide solution to convert the sulfides into elemental sulfur or alkali metal polysulfides in an electrochemical cell.

* * * * *